(12) United States Patent
Shin et al.

(10) Patent No.: US 7,504,117 B2
(45) Date of Patent: Mar. 17, 2009

(54) EXTRACT OF NELUMBINIS SEMEN FOR THE TREATMENT OF DEPRESSION

(75) Inventors: Min-Kyu Shin, Seoul (KR);
Moo-Chang Hong, Seoul (KR);
Hyeon-Su Bae, Seoul (KR);
Jeong-Hwan Yoon, Utwang-si (KR);
Moon-Kyu Kang, Namyangju-si (KR);
Jung-Wan Oh, Seongnam-si (KR)

(73) Assignee: Purimed Co., Ltd., Dongdaemun-Gu, Seoul (KR)

( * ) Notice: Subject to any disclaimer, the term of this patent is extended or adjusted under 35 U.S.C. 154(b) by 0 days.

(21) Appl. No.: 11/701,424

(22) Filed: Feb. 2, 2007

(65) Prior Publication Data
US 2007/0148265 A1    Jun. 28, 2007

Related U.S. Application Data

(63) Continuation of application No. 10/569,844, filed as application No. PCT/KR03/01743 on Aug. 28, 2003, now abandoned.

(51) Int. Cl.
*A01N 65/00* (2006.01)
*A61K 36/00* (2006.01)

(52) U.S. Cl. ...................... 424/725; 424/776

(58) Field of Classification Search ............. None
See application file for complete search history.

(56) References Cited

U.S. PATENT DOCUMENTS

| | | | | |
|---|---|---|---|---|
| 5,739,144 A * | 4/1998 | Warrellow et al. | .......... | 514/277 |
| 6,254,558 B1 * | 7/2001 | Meconi et al. | .......... | 602/6 |
| 6,602,526 B2 * | 8/2003 | Riley | .......... | 424/776 |
| 2002/0098253 A1 | 7/2002 | Riley | | |
| 2006/0216331 A1 * | 9/2006 | Lines | .......... | 424/440 |
| 2007/0059400 A1 * | 3/2007 | Goto et al. | .......... | 426/52 |

FOREIGN PATENT DOCUMENTS

| | | |
|---|---|---|
| CN | 1233486 A * | 12/1998 |
| CN | 1406624 | 4/2003 |
| FR | 2739531 A1 * | 4/1997 |
| JP | 08-295632 | 11/1996 |
| JP | 2002-029980 | 1/2002 |

(Continued)

OTHER PUBLICATIONS

Yu et al (Acta Pharmaceutica Sinica 32 (1): 1-4, 1997).*

(Continued)

*Primary Examiner*—Patricia Leith
*Assistant Examiner*—Qiuwen Mi
(74) *Attorney, Agent, or Firm*—Robert E. Bushnell, Esq.

(57) ABSTRACT

Provided is a method for treating depression with a Nelumbinis Semen extract. The Nelumbinis Semen extract is prepared by extracting Nelumbinis Semen with an alcohol or an alcohol solution. The Nelumbinis Semen extract has been demonstrated using animal behavioral, bio-chemical and molecular biological methods to have strong antidepressive activity, as well as inhibiting immune suppression caused by depression, leading to normal immune responses, and reducing side effects of conventional antidepressants, thereby ensuring safety. Thus, the Nelumbinis Semen extract is useful for preparing a composition or health food for treating depression.

14 Claims, 2 Drawing Sheets

FOREIGN PATENT DOCUMENTS

| | | |
|---|---|---|
| JP | 2002-068993 | 3/2002 |
| JP | 2003-113100 | 4/2003 |
| KR | 1020020015540 | 2/2002 |
| KR | 1020030079104 | 10/2003 |
| KR | 1020040026175 | 3/2004 |
| WO | WO 02/102397 | 12/2002 |

OTHER PUBLICATIONS

Durman et al (Neuropsychopharmacology 25 (6): 836-844, 2001).*

Vetulani et al (Antidepressants: past, present, and future, European Journal of Pharmacology 405 (2000) 351-363).*

Scott et al (Vasopressin as a target for antidepressant development: an assessment of the available evidence, Journal of Affective Disorders 72 (2002) 113-124).*

Maeda et al (Potential antidepressant properties of forskolin and a novel water-soluble forskolin (NKH477) in the forced swimming test, Life Science 61 (25): 2435-2442, 1997).*

Revilla et al., Comparison of several procedures used for the extraction of anthocyanins from red grapes, J. Agric. Food Chem. 46: 4592-4597, 1998.*

Phillipson, J., New drugs form nature-it could be yew, Phytotherapy Research, 13: 2-8, 1999.*

Persons et al., Persons et al, Anxiety and depression change together during treatment, Behavior Therapy 34: 149-163, 2003.*

Pulok K. Mukherjee et al., "Studies on psychopharmacological effects of *Nelumbo nucifera* Gaertn. Rhizome extract", Journal of Ethnopharmacology, 54, pp. 63-67, 1996.

Noboru Shoji et al., "Asimilobine and lirinidine, serotonergic receptor antagonists, from *Nelumbo nucifera*", In; J. Nat. Prod. 1987; 50(4): 773-4.

Abstract of Hasrat JA et al, "Isoquinoline derivatives isolated from the fruit of Annona muricata as 5-HT ergic 5-HT1A receptor agonists in rats: unexploited antidepressive (lead) products", J Pharm Pharmacol. Nov. 1997; 49(11): 1145-9.

Pulok K. Mukherjee et al., "Studies on psychopharmacological effects of *Nelumbo nucifera* Gaertn. rhizome extract", Journal of Ethnopharmacology 54 (1996) 63-67.

*Supplementary European Search Report* from the European Patent Office issued in Applicant's corresponding European Patent Application No. 03 81 8419 dated Dec. 4, 2006.

* cited by examiner

EXTRACT OF NELUMBINIS SEMEN FOR THE TREATMENT OF DEPRESSION

CROSS-REFERENCES TO RELATED APPLICATIONS

This application makes reference to, incorporates the same herein, and claims all benefits accruing under Title 35 U.S. Code §365(b)(c) of my PCT International application entitled EXTRACT OF NELUMBINIS SEMEN FOR THE TREATMENT OF DEPRESSION, filed on 28 Aug. 2003 and duly assigned Serial No. PCT/KR2003/001743. Further, this application is a Continuation of Applicant's patent application Ser. No. 10/569,844 filed in the U.S. Patent & Trademark Office on the 28 Feb. 2006, now abandoned and assigned to the assignee of the present invention. All benefits accruing under 35 U.S.C. §120 from the parent application are also hereby claimed.

BACKGROUND OF THE INVENTION (1) Field of the Invention

The present invention relates, in general, to an extract of Nelumbinis Semen (*Nelumbo nucifera*) having a therapeutic effect on depression, a method of preparing the extract, and a pharmaceutical composition and a health food comprising the extract. More particularly, the present invention relates to a Nelumbinis Semen extract obtained by extracting Nelumbinis Semen with an alcohol or an alcohol solution and concentrating and drying the resulting extract, a method of preparing the Nelumbinis Semen extract, and a pharmaceutical composition and a health food which comprise the Nelumbinis Semen extract as an effective component.

(2) Description of the Related Art

Mental damage occurring in the complicated modern society is, contrary to in the past, mostly caused by weak but prolonged and repeated stress from usual activities rather than large psychological impact or stimuli. Such stress is difficult to be recognized by patients and easily overlooked during hospital visits by patients, and thus accumulates, causing individuals to suffer from depression.

Depression is an emotional pathological phenomenon occurring regardless of objective situations. Emotional symptoms of depression include depressed behavior during all activities, anhedonia (loss of interest or pleasure), diminished mental capacity, pessimism, poor self-esteem, and suicidal thoughts that occasionally lead to suicide attempts. Physical symptoms of depression include decreased appetite, insomnia, constipation, diminished sexual desire, reduced immune functions, and patients' susceptibility to diseases due to the reduced immune function.

There has been so far no theory that perfectly explains the mechanism causing depression and the action mechanism of antidepressants for treating depression. However, for many years, the prevailing hypothesis is that depression is caused by an absolute or relative deficiency of monoamine neurotransmitters in synapses of the central nervous system, such as serotonin, norepinephrin and dopamine. In this regard, all antidepressants have pharmaceutical action to increase concentrations of neurotransmitters in central serotonin or noradrenaline synapses.

Antidepressants are divided into three major types according to the mechanism involving increasing the neurotransmitter levels: tricyclic antidepressants (TCA); monoamine oxidase inhibitors (MAOI); and selective serotonin reuptake inhibitors (SSRI).

Monoamine oxidase inhibitors, such as phenelzine developed a relatively long time ago, have a severe adverse effect of inducing heart diseases, and thus, have not been widely used recently. Tricyclic antidepressants such as imipramine also have anticholinergic, sedative, and other side effects related to the cardiovascular system. Thus, recent research focuses on the development of therapeutic agents against depression using selective serotonin (5-hydroxytryptamine, or 5-HT) reuptake inhibitors (hereinafter, referred to simply as "SSRI") as antidepressants with fewer side effects. Representative examples include fluoxetine (brand name: Prozac), paroxetine (brand name: Seroxate), and sertraline (brand name: Zoloft), which are widely approved due to their clinical efficacy. However, the aforementioned drugs also have side effects such as whole-body fatigue, sexual dysfunction and insomnia. Administration of antidepressants was reported to typically activate a serotonin receptor by increasing serotonin levels, leading to an activation of protein kinase A (PKA) that is downstream of the serotonin receptor and eventually increases in protein levels of cAMP response element-biding (CREB), brain-derived neurotrophic factor (BDNF) and its receptor, trkB. These increased protein levels are considered to indicate effective actions of antidepressants in molecular levels (*J. of Psychosomatic Research* 53, 687-697 (2002)). In addition, the administration of antidepressants restores to normal levels decreased concentrations of cortisol and interleukin-2 (IL-2) and decreased cell numbers of white blood cell (WBC) and lymphocytes, all of which are representative responses of individuals with depression, thereby providing a normal immune system (*Ann NY Acad Sci.* 917, 478-487 (2000)). These effects may be another therapeutic effect of antidepressants.

Recently, in the Western countries, medicinal herbal extracts have been recognized for their therapeutic effects and studied. With regard to depression, extracts of *Hypericum perforatum* (known also as St. John's wort) have been studied (*Neuropharmacology*, 1999, 21 (2), 247-257; Cochrane Database Syst Rev, 2000, (2), CD000448 ; Drugs Aging, 2000, 16 (3), 189-197).

According to a report that compared a *Hypericum perforatum* extract with imipramine for therapeutic efficacy on depression, the *Hypericum perforatum* extract has similar efficacy to imipramine in treating depression and has fewer side effects (*BMJ*, 2000, 321,536-539). Also, the *Hypericum perforatum* extract has the potential to inhibit the activities of human cytochrom P450 enzymes (*J Pharmacol Exp Ther*, 2000, 294(1), 88-95).

The *Hypericum perforatum* extract contains a large number of structurally different compounds that directly or indirectly affect the central nervous system (CNS). That is, the *Hypericum perforatum* extract contains bioactive compounds, such as hypericin and hyperforin, and dimeric flavors, which are known to have antidepressive and apprehension-removing effects in animals and humans.

The action mechanisms of the constituents of *Hypericum perforatum* are as follows. Hypericin is proved to have the antidepressive effect in the presence of dimeric procyanidins contained in the *Hypericum perforatum* extract (Regensburg, Germany, V. Butterwecke et. al.,45th *Annual Congress of the Society for Medicinal Plant Research*, 1997, Abstract No. 011). Hyperforin increases 5-HT (serotonin) levels in the hypothalamus and hippocampus, indicating that the antidepressive effect of hyperforin is associated with the serotonergic system (*J Pharm Pharmacol*, 2001, 53 (5), 583-600; Pharmacopsychiatry, 2000, 33(2), 60-65). However, about 20% of depression patients are not treated with conventional antidepressants, and recently developed antidepressants such as SSRI have fewer side effects than other antidepressants, but they are still not negligible.

On the other hand, various depression animal models have been tried in the development process of antidepressants for treating depression. Strong stimuli such as intense foot-shock, cold water immersion and 48 h food/water deprivation were initially preferred, but, recently, preferred methods are to use weak repetitive stresses better capable of mimicking usual activities of modern people experiencing weak prolonged chronic stresses (*Psychopharmacology*, 1984, 83, 1-16). Among the recent methods, a chronic mild stress (hereinafter, referred to simply as "CMS") model, suggested by Willner et al., has been approved as an excellent animal model of depression having reliability and validity (*Neuroscience and Biobehavial Review*, 1981, 5, 231-246; TIPS, 1991, 12, 131-136).

"Mildly stressed rats" means that, when CMS-induced behavioral changes are observed for a prolonged administration period of weeks, the behavioral changes do not occur habitually, or habitual changes occur within a constant limitation (*Psychopharmacology*, 1997, 134, 319-320). In general experiments, a variety of chronic weak stressors, such as overnight illumination, periods of food and/or water deprivation, cage tilt and change of cage mate, are used (*Psychopharmacology*, 1997, 134, 319-320). Repeated exposure of white rats to such stressors results in a significant decrease in consumption of a sucrose solution, which is comparable to anhedonia, the representative symptom of depression of white rats. Upon no appropriate treatment, such decrease in consumption of a sucrose solution is known to last for several weeks after withdrawal of a CMS procedure. Many antidepressants have been approved that they have effects of recovering the reduced sucrose intake induced by the CMS procedure to an original level (*Psychopharmacology*, 1992, 109, 433-438).

On the other hand, Nelumbinis Semen is the skinned ripe seed of lotus (*Nelumbo nucifera*), which has a green core. Nelumbinis Semen has no smell and a sweet, fresh and slightly astringent taste.

Nelumbinis Semen contains a large quantity of starch and raffinose sugar, and is known to have the therapeutic effects of strengthening the spleen and stomach, alleviating insomnia, whitening the skin, relieving inflammation and healing wounds in the skin. However, to date, there is no report of its ability to alleviate depression symptoms.

SUMMARY OF THE INVENTION

The present invention aims to provide a method for treating depression.

According to an aspect of the present invention, there is provided a method for treating depression comprising administering to a subject in need thereof an effective amount of a composition comprising an extract of Nelumbinis Semen.

The extract is preferably prepared by extracting Nelumbinis Semen with an alcohol or an alcohol solution.

According to still an aspect of the present invention, there is provided a method for increasing at least one selected from the group consisting of expression levels of cAMP response element-biding (CREB), brain-derived neurotrophic factor (BDNF) and trkB genes, protein levels of CREB, BDNF and trkB, levels of 5-hydroxytryptamine (5-HT) and norepinephrine (NE), and a binding of serotonin 2A receptor agonist, [$^3$H] spiperone in a subject comprising administering to the subject in need thereof an effective amount of a composition comprising an extract of Nelumbinis Semen.

According to another aspect of the present invention, there is provided a method for restoring at least one selected from the group consisting of: decreased cortisol concentration, decreased IL-2 concentration, decreased cell number of white blood cell, and decreased cell number of lymphocytes in a subject, comprising administering to the subject in need thereof an effective amount of a composition comprising an extract of Nelumbinis Semen.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE PREFERRED EMBODIMENTS

Based on the fact that Nelumbinis Semen is used as a Chinese traditional herbal medicine, the intensive and thorough animal behavioral research into the therapeutic effects of an extract of Nelumbinis Semen, conducted by the present inventors, resulted in the finding that the Nelumbinis Semen extract is superior in treating depression to conventional antidepressants, *Hypericum perforatum* extract and fluoxetine (brand name: Prozac) one of SSRI, the recently most commonly used antidepressants, thereby providing a pharmaceutical composition for treating depression comprising the Nelumbinis Semen extract of the present invention.

In addition, the molecular biological and biochemical research revealed the mechanism of the antidepressive action of the Nelumbinis Semen extract of the present invention, and resulted in the finding that the Nelumbinis Semen extract has another effect of normalizing immune functions, thereby providing a pharmaceutical composition for treating depression comprising the Nelumbinis Semen extract of the present invention.

Further, the animal behavioral research resulted in the finding that the Nelumbinis Semen extract of the present invention does not have the side effects that are observed upon application of conventional antidepressants.

Thus, in one aspect, the present invention provides a Nelumbinis Semen extract having antidepressive activity.

In another aspect, the present invention provides a method of preparing the Nelumbinis Semen extract.

In a further aspect, the present invention provides a pharmaceutical composition for treating depression, comprising the Nelumbinis Semen extract as-an effective component.

In yet another aspect, the present invention provides a health food for treating depression, comprising the Nelumbinis Semen extract as an effective component.

Hereinafter, the present invention will be described in detail.

The present invention provides a Nelumbinis Semen extract having antidepressive activity.

The Nelumbinis Semen extract of the present invention is prepared by a process including 1) extracting Nelumbinis Semen with an alcohol or an alcohol solution; 2) filtering and concentrating the resulting extract; and 3) freeze-drying the resulting concentrate.

The alcohol or alcohol solution may be selected from the group consisting of 10-100% ethyl alcohol and 10-100% methyl alcohol. Preferred is 70-100% ethyl alcohol.

The extraction is carried out by cold extraction (maceration), under reflux conditions or by ultrasonic treatment. The ultrasonic extraction is preferred.

The present inventors investigated that the Nelumbinis Semen extract of the present invention has antidepressive activity. After the Nelumbinis Semen extract of the present invention was administered, experimental animals were stressed by being exposed to bright light for a period of 48 hrs before a forced swim test. During forced swimming, the following behaviors were evaluated: struggling time (time spent struggling, defined as strongly moving all four limbs), first latency (latency until first floating) and first rest duration (length of the first floating). As a result, the Nelumbinis Semen extract of the present invention displayed antidepressive activity and had a higher antidepressive effect than a comparative group, *Hypericum perforatum* extract.

In addition, the present inventors compared the Nelumbinis Semen extract of the present invention with other Chinese medical herbs. The Chinese medical herbs as comparative subjects included Rehmanniae Radix Preparat, Lycii Fructus and Corni Fructus, which strengthen body functions, and Pinelliae Rhizoma that has an expectorating effect (Table 1).

TABLE 1

Chinese medical herbs and their amount used

| Chinese medical herb (Pharmaceutical name) | Amount |
| --- | --- |
| Rehmanniae Radix Preparat | 500 g |
| Corni Fructus | 500 g |
| Lycii Fructus | 500 g |
| Pinelliae Rhizoma | 500 g |
| Nelumbinis Semen | 500 g |
| *Hypericum perforatum* | 500 g |

As a result, the Nelumbinis Semen extract of the present invention was found to have a higher antidepressive effect than extracts of Rehmanniae Radix Preparat, Lycii Fructus, Corni Fructus and Pinelliae Rhizoma.

In addition, the Nelumbinis Semen extract of the present invention was tested for its antidepressive activity and for overcoming sexual dysfunction, which is a representative side effect of conventional antidepressants. In this test using the aforementioned CMS model of depression in rats, being applicable to practical situations, where rats were exposed to CMS to induce depression, the rats were administered with conventional antidepressants, Prozac and a *Hypericum perforatum* extract, and the Nelumbinis Semen extract of the present invention, antidepressive effects and side effects of the administered drugs were evaluated by objective comparison between test groups for behavioral changes including changes in weight, sucrose intake and physical activity in an open place. Also, a reduction in sexual behavior, which is a representative side effect of the SSRI depressants, was investigated by comparison between test groups for mating behavior according to the above drugs. As a result, the Nelumbinis Semen extract of the present invention was found to have a higher antidepressive effect than the comparative drugs, *Hypericum perforatum* extract and Prozac, while not displaying reduced sexual behavior that is a side effect of the above conventional antidepressive drugs, thereby indicating that the present Nelumbinis Semen extract does not have the side effects found upon the application of conventional antidepressive drugs.

Further, the mechanism of the antidepressive action of the Nelumbinis Semen extract of the present invention was assessed according to the following molecular biological and biochemical methods.

First, according to a molecular biological method, after a depression-induced experimental animal was administered with an effective amount of the Nelumbinis Semen extract of the present invention and the conventional antidepressive drugs, the experimental animal with improved depression was incised at the cerebral frontal cortex. Total RNA was isolated from the cerebral frontal cortex, and double-stranded cDNA was synthesized using the isolated RNA and an oligo (dT) 24-T7 primer. cRNA was synthesized by in vitro transcription using the synthesized cDNA, and was biotin-labeled and applied to an oligonucleotide microarray to determine gene expression patterns in each test group. As a result, the Nelumbinis Semen extract of the present invention was found, like the *Hypericum perforatum* extract and Prozac used as comparative drugs, to significantly increase expression levels of CREB, BDNF and trkB genes that are representative in vivo markers of antidepression.

Also, according to a biochemical method, the therapeutic efficacy of a candidate drug was primarily examined by measuring changes in 5-HT and Norepinephrine (NE) levels in a chronic CMS model by microdialysis and HPLC-ECD. Catecholamine content was measured using an HPLC system equipped with an electrochemical detector. A mobile phase containing 0.05 M monobasic sodium phosphate, 0.1 N sodium acetic acetate and 1% methanol was adjusted to pH 4.4 with a phosphate buffer for HPLC. DA was composed of a Supelcosil LC-8-DB 3-µm column (150×4.6 mm, Supelco, Bellefonte, Pa.) protected by an LC-18 guard column. As a result, the Nelumbinis Semen extract of the present invention was found, like the *Hypericum perforatum* extract and Prozac used as comparative drugs, to significantly increase levels of the 5-HT and NE neurotransmitters.

Secondarily, antidepressive effects were evaluated by an increase or decrease in receptor binding of a serotonin 2A receptor agonist, [$^3$H] spiperone, in the rat brain frontal cortex, as follows. A behavioral test in rats was carried out for a period of three weeks, and the rats were administered with each drug. The brain frontal cortex was excised from the rats and frozen in liquid nitrogen. The frontal cortex was cryo-sectioned into a horizontal form using a cryostat microtome, and each section was incubated in a[$^3$H] spiperone-containing Tris-HCl buffer for two hours, dried, placed in an autoradiography cassette and exposed to an autoradiography film for four weeks in a refrigerator. Then, the film was developed and scanned with a densitometer to measure light and dark intensity that corresponds to binding strength. After calibrated values were calculated using a standard scale bar, binding strength of each cryo-section was expressed as Ci/mg tissue. When test groups were compared with a control group for an increase or decrease in receptor binding as an indication of antidepressive action, the Nelumbinis Semen extract of the present invention was found, like the *Hypericum perforatum* extract and Prozac used as comparative drugs, to significantly increase the binding of the serotonin 2A receptor agonist, [$^3$H] spiperone.

Thirdly, an increase in the antidepressive markers, CREB, BDNF and trkB proteins, was examined in the rat cerebral frontal cortex by Western blotting, as follows. A behavioral test in rats was carried out for a period of three weeks, and the rats were administered with each drug. The brain frontal cortex was excised and centrifuged, and the supernatant was recovered. Each sample was mixed with a SDS-PAGE sample buffer to reduce proteins and boiled to denature proteins. Samples were loaded onto a SDS-PAGE (sodium dodecyl sulfate poly acrylamide gel electrophoresis) gel and run at 100-200 V for about 1-2 hrs. The SDS-PAGE gel was transferred onto a PVDF or nitrocellulose membrane by electro-transferation. The membrane was incubated with a primary antibody for a target protein, washed and incubated with a secondary antibody. Then, the target protein was detected by an enhanced chemiluminescent method. As a result, the Nelumbinis Semen extract of the present invention was found, like the *Hypericum perforatum* extract and Prozac used as comparative drugs, to significantly increase protein levels of CREB, BDNF and trkB.

Fourthly, an increase in the antidepressive markers, CREB, BDNF and trkB proteins, was examined in the rat cerebral frontal cortex by 2-DE, as follows. A behavioral test in rats was carried out for a period of three weeks, and the rats were administered with each drug. The brain frontal cortex was excised and centrifuged, and the supernatant was recovered. Each sample was mixed with an IEF sample buffer and loaded onto an IEF gel. Proteins were separated according to isoelectric point by isoelectric focusing (IEF) in the first dimension and according to molecular weight by SDS-PAGE at 100-200 V for about 1-2 hrs in the second dimension. The gel was stained by a Gel-Code Blue staining method and evaluated for elevated or newly emerged proteins by the antidepressive substances. The elevated or newly emerged proteins by the antidepressive substances were subjected to mass spectrometry. As a result, the Nelumbinis Semen extract of the present invention was found, like the *Hypericum perforatum* extract and Prozac used as comparative drugs, to significantly increase protein levels of CREB, BDNF and trkB.

In addition, the Nelumbinis Semen extract of the present invention was evaluated to determine its ability to help overcome immune suppression caused by depression, by the following biochemical method.

First, changes in concentrations of cortisol, which is a representative marker to determine whether the immune suppression has been overcome, according to administration of the Nelumbinis Semen extract were examined, as follows. After urine samples were collected from rats, (1) 1.0 ml of urine was placed into a tube with a cap, 2.0 ml dichloromethane was added to the tube, and the tube was covered with the cap with caution;

(2) the mixture was vortexed for 5-10 min;

(3) the mixture was centrifuged at 1500×g (rpm), the upper layer was aspirated, and 50 µl of the lower layer were aliquotted into coated tubes;

(4) samples were evaporated for dryness.

Urinary cortisol concentrations were measured as follows.

(1) The coated tubes were individually labeled with NSB, Std (A-F), a control (CON6 No. 5) and sample numbers (for NSB, a green tube was used).

(2) 25 µl of each of NSB, Std(A-F), a control (CON6 No. 5) and samples was added to the corresponding tube (free cortisol was added to the completely dried coated tube, and 25 µl of Std. A was added to the NSB tube).

(3) 1.0 ml of $^{125}$I-cortisol was added to the tubes, followed by mixing.

(4) The tubes were incubated in a water bath at 37° C. for 45 min and aspirated.

(5) After the content of the tubes was completely aspirated, radioactivity was measured for at least 1 min using a Y-counter.

As a result, the Nelumbinis Semen extract of the present invention was found, like the *Hypericum perforatum* extract and Prozac used as comparative drugs, to restore cortisol concentrations to levels similar to a normal group.

Secondarily, changes in concentrations of IL-2, which is a representative marker to determine whether the immune suppression has been overcome, according to administration of the Nelumbinis Semen extract was examined, as follows. After blood samples were collected from rats, (1) 100 µl of assay diluent QD6-23 were aliquotted onto a microplate strip;

(2) 50 µl of each sample and a standard were aliquotted onto the strip;

(3) the strip was incubated with shaking at room temperature for 2 hrs;

(4) the strip was washed four times;

(5) 200 µl of an IL-2 conjugate was aliquotted onto the strip, and the strip was incubated with shaking at room temperature for 3 hrs;

(6) 200 µl of a substrate (luminol+hydrogen peroxide) was aliquotted onto the strip, and the strip was incubated at room temperature for 20-40 min;

(7) emitted light was measured using a luminometer; and (8) IL-2 concentrations were determined using a standard quantitative curve.

As a result, the Nelumbinis Semen extract of the present invention was found, like the *Hypericum perforatum* extract and Prozac used as comparative drugs, to restore IL-2 concentrations to levels similar to a normal group.

Thirdly, changes in WBC cell number, which is a representative marker to determine whether the immune suppression has been overcome, according to administration of the Nelumbinis Semen extract, was examined, as follows. After blood samples were collected from rats, cell volume, conductivity and light scattering were measured.

1) Cell Volume

Cell volume was measured according to the Coulter Principle, which is universally recognized as a reference method for sizing of volumes. An aperture between two electrodes is placed in a cell flow, and direct current flows between the electrodes. When WBC maintained at nearly natural states passes through the aperture, electrical resistance to the direct current flow increases, thus generating a voltage pulse being in proportion to cell volumes. The size of the pulse is one of the distinct features allowing determination of the type of WBC. However, to distinguish between two types of cells with similar size, a different phenotype allowing the distinction of two types of cells should be measured. For example, mature basophils and small lymphocytes are about 9-12 jjm in diameter, and immature prolymphocytes and mature neutrophils are 12-14 μm in diameter. Different types of cells with similar size are difficult to determine based on only their size, and thus, in this case, conductivity and light scattering are simultaneously measured.

2) Conductivity

Conductivity measurement is based on measuring cell contents using a high-frequency electromagnetic field. This technology is a method of measuring cell contents, which started to be developed in the 1960s by Doctor Wallace Coulter, the founder of the Coulter Electronics Company, and was patented in USA in 1970. Doctor Coulter demonstrated that a high-frequency current is able to penetrate the cell membrane. The current that has penetrated cells exists in specific forms according to the composition of the nucleus and granules and the internal chemical composition of cells. The application of this high-frequency electromagnetic field creates a novel practical method capable of providing information about contents of cells. Doctor Coulter suggested a very important, new measurement item called "opacity", which has information about composition of the cytoplasm and the nucleus in an electromagnetic field where a high-frequency current penetrates cells. "Opacity" is a conductivity signal reflecting the internal composition of cells, which is not influenced by cell size. "Opacity" measurement provided only by the Coulter Company is the most accurate and reliable technology for measuring cell contents. Conductivity is useful for separating cells of similar size, but different internal composition. Only volume measurement does not distinguish basophils from small lymphocytes. However, since conductivity measurement is carried out by measuring the difference between cell types in the ratio of the nucleus to the cytoplasm, granularity, etc., it is very useful for separating cell types.

3) Light Scattering

In addition to volume and conductivity data, light scattering characteristics on the cell surface distinctly differ between cell types. Homogeneous light emitted from a laser is collected using a lens and converted to a voltage pulse. Thus, light scattering is very useful for sorting cells according to the morphology and amount of granules.

WBC counting using the above methods resulted in the finding that the Nelumbinis Semen extract of the present invention was found, like the *Hypericum perforatum* extract and Prozac used as comparative drugs, to restore the cell number of WBC to levels similar to a normal group.

Fourthly, changes in cell number of lymphocytes, which is a representative marker to determine whether the immune suppression has been overcome, according to administration of the Nelumbinis Semen extract, was examined as follows. After blood samples were collected from rats, changes in lymphocyte cell number were examined by the following method.

1. Assay Principle

When diluted blood corpuscles are suspended in an electrolyte solution (Isoton sol.) that is a separate insulator, the electrolyte suspension of particles is suctioned for 4 sec through an aperture with a predetermined size. The aperture is placed between an internal electrode and an external electrode, and a current flows between the electrodes. When particles pass through the aperture between the two electrodes, resistance increases while voltage decreases. The difference between decreased voltage and ground voltage is expressed as height by a threshold circuit. The number of pulses indicates the number of particles, and the amplitude of pulses is in proportion to the volume of corpulscles.

2. Assay Method: Automatic Analyzer
3. Machine Used: ADVIA120, Bayer, USA
4. Reagents Used:
   1) Isoton III, Beckman Coulter, USA
   2) Coulter clenz, Beckman Coulter, USA
   3) Lyse S III, Beckman Coulter, USA
   4) 4% sod. hypochloride-solution, Beckman Coulter, USA
   5) 4C-plus, Beckman Coulter, USA
   6) Scatter Pak, Beckman Coulter, USA As a result, the Nelumbinis Semen extract of the present invention was found, like the *Hypericum perforatum* extract and Prozac used as comparative drugs, to restore the cell number of lymphocytes to levels similar to a normal group.

In addition, the present invention provides a pharmaceutical composition for treating depression, comprising the Nelumbinis Semen extract as an effective component.

The present pharmaceutical composition for treating depression includes the Nelumbinis Semen extract as an effective component. The pharmaceutical composition may be administered orally or parenterally and may be formulated into typical pharmaceutical preparations.

That is, the Nelumbinis Semen extract of the present invention may be formulated into various formulations for oral and parenteral administration upon clinical application. In the formulation, diluents or excipients maybe used, which are exemplified by fillers, thickeners, binders, humectants, disintegrators and surfactants.

Examples of solid formulations for oral administration include tablets, pills, powders, granules and capsules. The solid formulations may include, in addition to the Nelumbinis Semen extract, at least one excipient selected from among starch, calcium carbonate, sucrose, lactose, gelatin, etc. Also, the solid formulations may include, in addition to a simple excipient, a lubricant such as magnesium stearate or talc.

Examples of liquid formulations for oral administration include suspensions, internal solutions, emulsions and syrups. The liquid formulations may include, in addition to commonly used simple diluents such as water and liquid paraffin, various excipients which are exemplified by humectants, sweeteners, aromatics and preservatives.

Examples of preparations for parenteral administration include sterile aqueous solutions, non-aqueous solutions, suspensions, emulsions, freeze-dried preparations and suppositories. In the formulation into non-aqueous solutions and suspensions, propylene glycol, polyethylene glycol, vegetable oils such as olive oil, and injectable esters such as ethyl oleate may be used. As a base of suppositories, witepsol, macrogol, Tween 61, cacao fat, lanolin fat, glycerol and gelatin may be used.

The unit dose, may, for example, occur one, two, three or four times, or a half, third or quarter of an individual dose. The individual dose preferably contains the amount of an effective drugs which is given in one administration and usually corresponds to a whole daily dose or a half, third or quarter of the daily dose.

In the pharmaceutical composition for treating depression, an effective amount of the Nelumbinis Semen extract ranges from 30 to 700 mg/kg, and preferably 100 to 500 mg/kg, and may be administered once to six times daily. The dosage for a specific patient may vary according to the patient's weight, age, sex, health state and diet, administration duration, administration routes, excretion rates and severity of the illness.

When the Nelumbinis Semen extract of the present invention was orally, intraperitoneally and subcutaneously administered to white rats to evaluate its toxicity, 50% lethal dose (LD50) of the Nelumbinis Semen extract upon the intraperitoneal administration was higher than 20 g/kg. This result demonstrates that the Nelumbinis Semen extract is safe.

In addition, the present invention provides a health food for treating depression, comprising the Nelumbinis Semen extract as an effective component.

In the case of using the present extract as a food, the present extract may be added as it exists or in combination with other food or food ingredients, and may be used suitably according to general methods. Mixed amounts of effective components may be suitably determined according to the intended use (preventive, health or therapeutic purposes). Typically, the present extract may be added in an amount of 0.01 to 1 wt %, and preferably 0.1 to 1 wt %, based on the total weight of raw materials used in preparing a food or drink. An effective amount of the present extract may be determined based on an effective amount of the pharmaceutical composition. When consumed for a long period of time for health and sanitary purposes or health control, the present extract may be used in an amount lower than the range. Also, it is apparent that the present extract can be used in an amount higher than the range because the effective component carries no safety risk.

The type of the food is not particularly limited. Examples of foods to which the present extract can be added include meats, sausages, breads, chocolates, candies, snacks, confectionary, pizza, instant noodles, other noodles, gums, dairy products including ice creams, various soups, beverages, teas, drinks, alcoholic beverages and vitamin complexes, as well as traditional therapeutic preparations for use as an antianemic, a body function-strengthening agent, a skin whitening agent, and the like. In addition, the present invention may be used in various prescriptions of Chinese medical decoctions, such as Reu Do Han Shao Tang, Quing Sin Shan Yao Tang and Tai Yin Tiao Wei Tang.

A better understanding of the present invention may be obtained, in conjunction with the accompanying drawings, through the following examples and experimental examples which are set forth to illustrate, but are not to be construed as the limit of the present invention.

EXAMPLE 1

Preparation of Nelumbinis Semen Extract 500 g of Nelumbinis Semen dried powder was placed into a flask containing 1 L of 70% ethyl alcohol and subjected to ultrasonic extraction (Branson Colo., USA) at room temperature for 10 min, and the supernatant was recovered. The pellet was further extracted with 85% and 100% ethylalcohol according to the same method as described above. The supernatants were pooled and filtered through a gauze. The filtrate was concentrated using a vacuum filter (Eyela, Japan) and freeze-dried, thus yielding 95 g of a Nelumbinis Semen extract according to the present invention.

EXPERIMENTAL EXAMPLE 1

Evaluation of Antidepressive Activity of the Nelumbinis Semen Extract

The Nelumbinis Semen extract of the present invention was orally administered to postnatal 85-95-day Sprague-Dawley male rats. A comparative group was orally administered with a *Hypericum perforatum* extract. For 48 hrs before a forced swim test, the rats were stressed by being exposed to bright light (300 Lux).

A forced swim test was carried out as follows. On day 1, the white rats were placed into a cylindrical water bath (22 cm in diameter; 30 cm water depth) and forced to swim for 10 min. On day 2, the rats were forced to swim for 5 min, and during this forced swimming, struggling time was measured.

Figure 1:
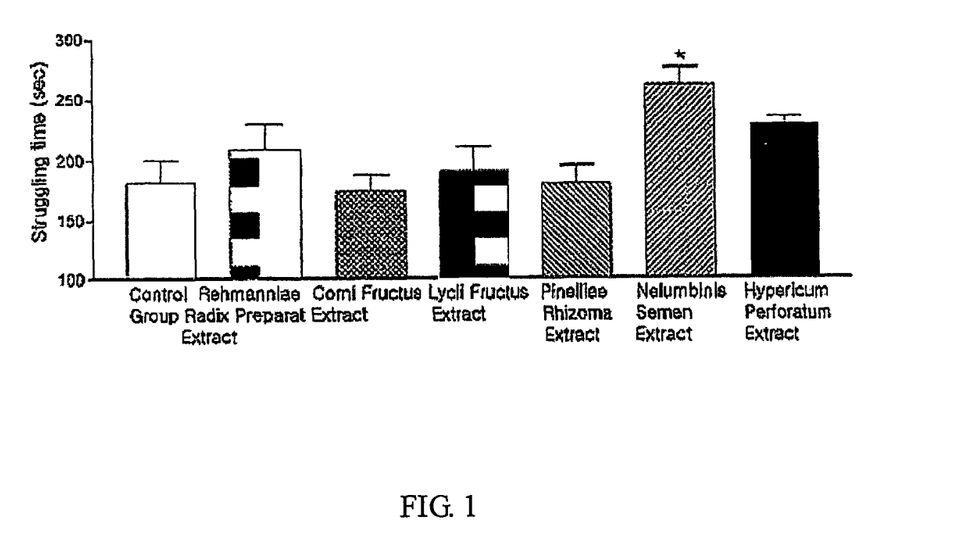
FIG. 1 is a graph showing the struggling time measured in a forced swim test using white rats, in which, for struggling time, a test group administered with a Nelumbinis Semen extract according to the present invention is compared to a control group and other test groups individually administered with a Rehmanniae Radix Preparat extract, a Corni Fructus extract, a Lycii Fructus extract, a Pinelliae Rhizoma extract and a *Hypericum perforatum* extract.

As a result, during the forced swimming, the comparative group administered with the *Hypericum perforatum* extract showed a non-significant increase in struggling time by 25.2% in comparison with a control group. In contrast, the Nelumbinis Semen extract significantly increased the struggling time by 43.9% (FIG. 1).

Figure 2:
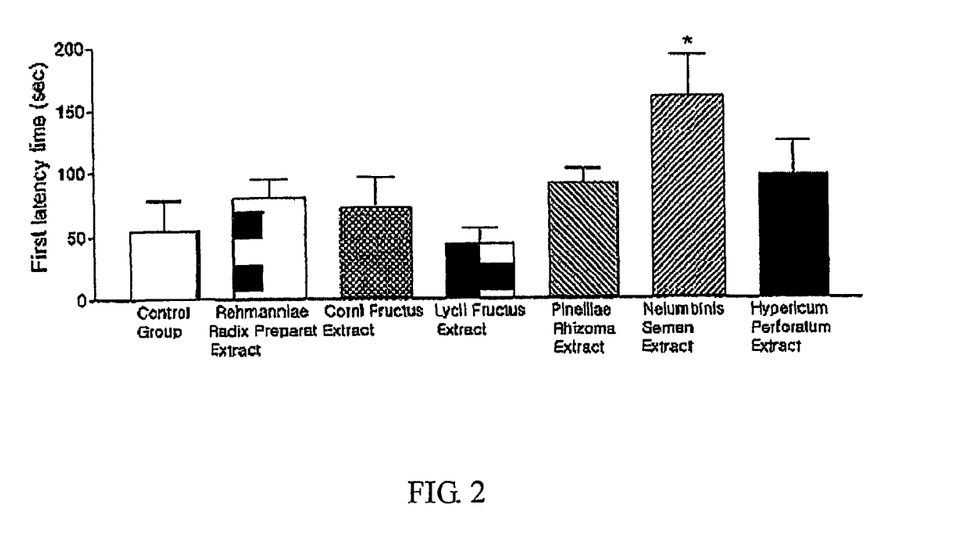
FIG. 2 is a graph showing the first latency time measured in a forced swim test using white rats, in which, for first latency time, a test group administered with a Nelumbinis Semen extract according to the present invention is compared to a control group and other test groups individually administered with a Rehmanniae Radix Preparat extract, a Corni Fructus extract, a Lycii Fructus extract, a Pinelliae Rhizoma extract and a *Hypericum perforatum* extract.

In addition, compared to the control group, administration of the *Hypericum perforatum* extract resulted in a non-significant increase in first latency time by 75.8%. In contrast, the Nelumbinis Semen extract significantly increased the first latency time by 90.2% (FIG. 2).

Figure 3:
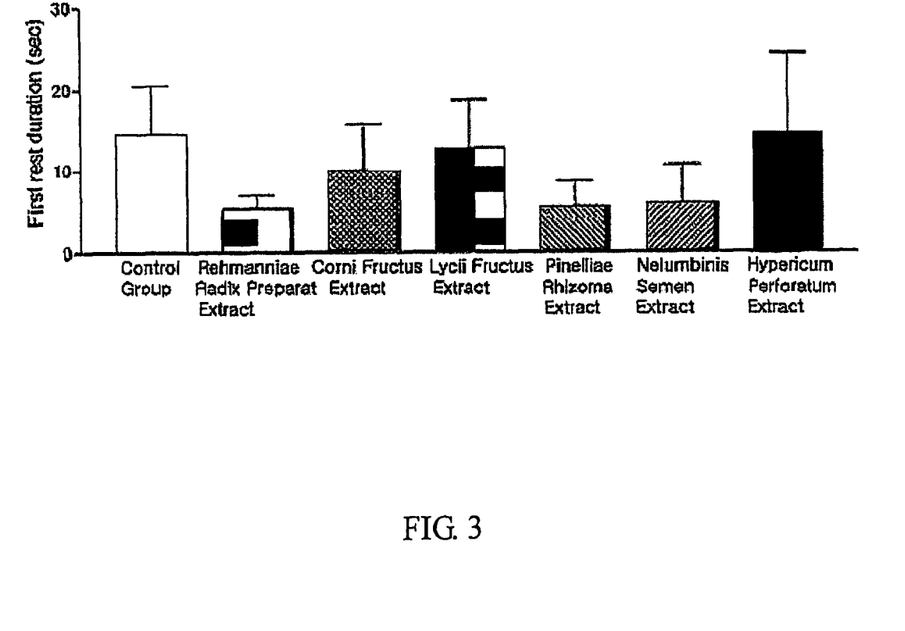
FIG. 3 is a graph showing the first rest duration measured in a forced swim test using white rats, in which, for first rest duration, a test group administered with a Nelumbinis Semen extract according to the present invention is compared to a control group and other test groups individually administered with a Rehmanniae Radix Preparat extract, a Corni Fructus extract, a Lycii Fructus extract, a Pinelliae Rhizoma extract and a *Hypericum perforatum* extract.

Further, compared to the control group, in the comparative group administered with the *Hypericum perforatum* extract, no change was observed in first rest duration. In contrast, in the group administered with the Nelumbinis Semen extract, the first rest duration decreased by 59.0% (FIG. 3).

These results indicate that the Nelumbinis Semen extract of the present invention has antidepressive activity and is superior to the *Hypericum perforatum* extract used as a comparative group in counteracting depression.

COMPARATIVE EXAMPLE

Comparison of the Nelumbinis Semen Extract with Other Chinese Medicinal Herbal Extracts for Antidepressive Activity The antidepressive effect of the Nelumbinis Semen extract was examined according to the same method as in Experimental Example 1 and compared with other Chinese medicinal herbal extracts of Rehmanniae Radix Preparat, Corni Fructus, Lycii Fructus and Pinelliae Rhizoma.

As a result, during the forced swimming, in comparison with a control group, administration of the Rehmanniae Radix Preparat and Lycii Fructus extracts resulted in a non-significant increase in struggling time by 15.2% and 4.9%, respectively, while administration of the Corni Fructus and Pinelliae Rhizoma extracts resulted in a reduction of 3.9% and 1.1%, respectively. In contrast, the Nelumbinis Semen extract significantly increased the struggling time by 43.9% (FIG. 1).

In addition, compared to the control group, administration of the Rehmanniae Radix Preparat, Corni Fructus and Pinelliae Rhizoma extracts resulted in an insignificant increase in first latency time by 38.4%, 29.2% and 65.5%, respectively, while administration of the Lycii Fructus extract resulted in a reduction of 21.4%. In contrast, the Nelumbinis Semen extract significantly increased the first latency time by 90.2% (FIG. 2).

Further, compared to the control group, administration of the Rehmanniae Radix Preparat, Corni Fructus, Lycii Fructus and Pinelliae Rhizoma extracts resulted in a reduction of 63.1%, 31.6%, 12.4% and 62.4%, respectively, in first rest duration. In contrast, administration of the Nelumbinis Semen extract resulted in a reduction of 59.0% in first rest duration (FIG. 3).

These results indicate that the Nelumbinis Semen extract of the present invention has higher antidepressive activity than the Rehmanniae Radix Preparat extract.

EXPERIMENTAL EXAMPLE 2

Evaluation of Acute Toxicity of the Nelumbinis Semen Extract Upon Oral Administration to Rats An acute toxicity test was carried out using 6-week specific pathogen-free(SPF) SD rats. The Nelumbinis Semen extract of the present invention was suspended in a 0.5% methylcellulose solution and orally administered to groups each consisting of five rats in a single dose of 5 g/kg, 10 g/kg and 20 g/kg. After administration of the extract, death, clinical symptoms and weight change were observed, and a hematological test and hematobiochemical analysis were performed. Upon autopsy, abnormality in abdominal organs and chest organs was visually observed.

As a result, all rats administered with the extract exhibited no particular clinical symptoms, no death, no change in weight and no toxicity upon the hematological assay, hematobiochemical analysis and autopsy. As a result, the Nelumbinis Semen extract of the present invention exhibited no toxicity even at a dose of 10 g/kg in all rats, and thus had a 50% lethal dose (LD50) higher than 20 g/kg upon oral administration. This result demonstrates that the Nelumbinis Semen extract is safe.

FORMULATION EXAMPLE 1

Preparation of Soft Capsules

Soft capsules were prepared according to a soft capsule preparation method described in General Rules for Preparation in a guidebook, Korean Pharmacopoeia, using 100.0 mg per capsule of the Nelumbinis Semen extract prepared in Example 1, 175.0 mg of soybean oil, 45.0 mg of cera flava, 127.5 mg of hydrogenated palm oil, 21.0 mg of soybean phospholipids, 212.0 mg of gelatin, 50.0 mg of glycerin (gravity: 1.24), 76.0 mg of di-sorbitol, 0.54 mg of methylparaoxybenzoate, 0.90 mg of propylparaoxybenzoate, 0.56 mg of methylvanillin, and a proper amount of yellow no. 203.

FORMULATION EXAMPLE 2

Preparation of Tablets 100.0 mg of the Nelumbinis Semen extract prepared in Example 1, 90.0 mg of corn starch, 175.0 mg of lactose, 15.0 mg of L-hydroxypropylcellulose, 5.0 mg of polyvinylpyrolidone 90 and a proper amount of ethanol were homogeneously mixed, granulated by wet granulation, mixed with 1.8 mg of magnesium stearic acid, and forced into 400 mg tablets.

FORMULATION EXAMPLE 3

Preparation of Capsules 100.0 mg of the Nelumbinis Semen extract prepared in Example 1, 83.2 mg of corn starch, 175.0 mg of lactose and 1.8 mg of magnesium stearic acid were homogeneously mixed, and filled into capsule shells at 360 mg per capsule.

FORMULATION EXAMPLE 4

Preparation of Food and Beverage

The present inventors prepared food and a beverage comprising the Nelumbinis Semen extract as an effective component, as follows.

<4-1> Preparation of Chewing Gum

Chewing gum was prepared according to a general method using 0.24-0.64% of the Nelumbinis Semen extract prepared in Example 1, 20% of gum base, 76.36-76.76% of sugar, 1% of a fruit aromatic and 2% of water.

<4-2> Preparation of Ice Cream

Ice cream was prepared according to a general method using 0.24-0.64% of the Nelumbinis Semen extract prepared in Example 1, 10.0% of milk fat, 10.8% of SNF (Solids Not Fat), 12.0% of sugar, 3.0% of starch syrup, 0.5% of an emulsion stabilizer (span), 0.15% of an aromatic (strawberry) and 63.31-62.91% of water.

<4-3> Preparation of Beve3rage

A beverage was prepared according to a general method using 0.48-1.28 mg of the Nelumbinis Semen extract prepared in Example 1, 522 mg of honey, 5 mg of thioctic acid amide, 10 mg of nicotinic acid amide, 3 mg of riboflavin hydrochloride sodium, 2 mg of pyridoxine hydrochloride, 30 mg of inositol, 50 mg of orotic acid and 200 ml of water.

<4-4> Preparation of Sausage

Sausage was prepared according to a general method using 0.24-0.64% of the Nelumbinis Semen extract prepared in Example 1, 63.6% of pork, 27.5% of chicken, 3.5% starch, 1.7% of soybean proteins, 1.62% of edible salt, 0.5% of glucose and 0.94-1.34% of another additive (glycerin).

As described hereinbefore, the Nelumbinis Semen extract of the present invention has very strong antidepressive activity, and Nelumbinis Semen, as the raw material of the Nelumbinis Semen extract, is a natural raw material used in Chinese medicine that is not harmful to the body and is well absorbed by the body when used as a pharmaceutical composition for treating depression. Therefore, the Nelumbinis Semen extract is very useful for treating and preventing depression and various related diseases.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for treating depression comprising administering to a subject in need thereof an effective amount of a composition comprising an extract of Nelumbinis Semen prepared by extracting Nelumbinis Semen with an alcohol or an alcohol solution.

2. The method according to claim 1, wherein the alcohol or alcohol solution is selected from the group consisting of 10-100% ethyl alcohol and 10-100% methyl alcohol.

3. The method according to claim 2, wherein the alcohol or alcohol solution is 70-100% ethyl alcohol.

4. The method according to claim 1, wherein the extract is prepared by extracting the Nelumbinis Semen with the alcohol or the alcohol solution, and filtering and concentrating a resulting extract.

5. The method according to claim 4, wherein the extraction of Nelumbinis Semen is selected from the group consisting of cold extraction, reflux extraction and ultrasonic extraction.

6. The method according to claim 1, wherein the extract is prepared by extracting the Nelumbinis Semen with the alcohol or the alcohol solution, filtering and concentrating a resulting extract, and freeze-drying a resulting concentrate.

7. The method according to claim 1, wherein the composition is administered orally, parenterally, intraperitoneally or subcutaneously.

8. The method according to claim 1, wherein the composition is in the form of a food, dietary supplement, or medicine.

9. The method according to claim 1, wherein the composition is a solid formulation in the form selected from the group consisting of tablets, pills, powders, granules and capsules.

10. The method according to claim 9, wherein the solid formulation further comprises at least one excipient selected from the group consisting of starch, calcium carbonate, sucrose, lactose, and gelatin.

11. The method according to claim 1, wherein the composition is a liquid formulation in the form selected from the group consisting of suspensions, internal solutions, emulsions and syrups.

12. The method according to claim 11, wherein the liquid formulation further comprises a diluent and optionally an excipient.

13. The method according to claim 1, wherein the composition is sterile aqueous solution, non-aqueous solution, suspension, emulsion, freeze-dried preparation or suppository.

14. The method according to claim 1, wherein the subject is human.

* * * * *